United States Patent [19]
Asakura et al.

[11] Patent Number: 4,762,604
[45] Date of Patent: Aug. 9, 1988

[54] OXYGEN CONCENTRATION SENSING APPARATUS

[75] Inventors: Masahiko Asakura; Noritaka Kushida; Takanori Shiina; Shin'ichi Kubota, all of Wako, Japan

[73] Assignee: Honda Giken Kogyo Kabushiki Kaisha, Tokyo, Japan

[21] Appl. No.: 28,113

[22] Filed: Mar. 19, 1987

[30] Foreign Application Priority Data

Mar. 19, 1986 [JP] Japan .................. 61-63204

[51] Int. Cl.⁴ ............................................. G01N 27/58
[52] U.S. Cl. .................................... 204/406; 204/412; 204/425
[58] Field of Search .................. 204/406, 15, 410–412, 204/425–426, 427

[56] References Cited

U.S. PATENT DOCUMENTS

| | | | |
|---|---|---|---|
| 4,440,621 | 4/1984 | Kitahara | 204/406 |
| 4,578,171 | 3/1986 | Yamada et al. | 204/406 |
| 4,586,476 | 5/1986 | Asayama | 123/440 |
| 4,594,139 | 6/1986 | Asayama et al. | 204/410 |
| 4,601,809 | 7/1986 | Kitahara | 204/406 |
| 4,609,452 | 9/1986 | Shimomura | 204/425 |
| 4,622,125 | 11/1986 | Oyama et al. | 204/406 |
| 4,622,126 | 11/1986 | Shimomura | 204/426 |
| 4,702,816 | 10/1987 | Hashimoto | 204/406 |

FOREIGN PATENT DOCUMENTS 8103410  3/1982  United Kingdom .

Primary Examiner—John F. Niebling
Assistant Examiner—Ben C. Hsing
Attorney, Agent, or Firm—Birch, Stewart, Kolasch & Birch

[57] ABSTRACT

An oxygen concentration sensing apparatus includes an oxygen pump element and a sensor cell element with a pair of electrodes respectively, being disposed to face each other, to form a restricted region between them, and a current source for supplying a pump current across the electrodes the oxygen pump element. A limit voltage is adjustably set in response to a voltage across the electrodes of the oxygen pump element, and the pump current supplied to the oxygen pump element is reduced when a voltage generated across the electrodes of the sensor cell element has exceeded the limit voltage.

2 Claims, 3 Drawing Sheets

OXYGEN CONCENTRATION SENSING APPARATUS

BACKGROUND OF THE INVENTION

1. Field of the Invention

The present invention relates to an oxygen concentration sensing apparatus, and more particularly to an oxygen concentration sensing apparatus for sensing an oxygen concentration in an exhaust gas of an internal combustion engine.

2. Description of Background Information

In order to accelerate the purification of the exhaust gas and to improve the fuel economy of an internal combustion engine, a feedback type air/fuel ratio control system is used, in which oxygen concentration in the exhaust gas is detected and air/fuel ratio of the mixture supplied to the engine is controlled to a target air/fuel ratio by a feedback control operation in accordance with a result of the detection of the oxygen concentration.

As an oxygen concentration sensor for use in such an air/fuel ratio control system, there is a type of sensor which is capable of producing an output signal whose level is proportional to the oxygen concentration in the exhaust gas of the engine, and the detail of which is disclosed in Japanese Patent Application laid open No. 58-153155. This oxygen concentration sensor includes an oxygen concentration sensing unit having a general construction including a pair of flat solid electrolyte members having oxygen ion permeability. These oxygen ion conductive solid electrolyte members are placed in the gas under measurement of the engine, and electrodes are respectively provided on the front and back surfaces of both of the solid electrolyte members. In other words, each pair of electrodes sandwich each solid electrolyte member. These two solid electrolyte members each having a pair of electrodes are arranged in parallel so as to face each other and forming a gap portion, or in other words, a restricted region between them.

With this arrangement, one of the solid electrolyte members serves as an oxygen pump element and the other one of the solid electrolyte members serves as a sensor cell element for sensing an oxygen concentration ratio. In an ambient atmosphere of the gas under measurement, a drive current is supplied across the electrodes of the oxygen pump element in such a manner that the electrode facing the gap portion operates as a negative electrode. By the supply of this current, i.e. a pump current, the oxygen component of the gas in the gap portion is ionized on the surface of the negative electrode of the oxygen pump element. The oxygen ions migrate through the inside of the oxygen pump element to the positive electrode, where the oxygen ions are released from the surface thereof in the form of the oxygen gas.

While this movement of the oxygen ions is taking place, the oxygen concentration becomes different for the gas in the gap portion and the gas outside the sensor cell element because of a decrease of the oxygen gas component in the gap portion. Therefore, if a current to the oxygen pump element, i.e. the pump current is maintained constant, a voltage proportional to the difference of the oxygen concentration, that is the oxygen concentration in the gas under measurement, develops across the electrodes of the sensor cell element. By this voltage generated at the sensor cell element, whether the air/fuel ratio of the mixture supplied to the engine is rich or lean with respect to a target air/fuel ratio can be determined. In the case of the air/fuel ratio control by means of the secondary air, the secondary air is supplied to the engine when the air/fuel ratio is detected to be rich. On the other hand, the supply of the secondary air is stopped when the air/fuel ratio is detected to be lean. In this way, the air/fuel ratio of the mixture is controlled toward the target air/fuel ratio. If the magnitude of the pump current supplied to the oxygen pump element is controlled so that the voltage generated across the sensor cell element is maintained constant, the magnitude of the pump current varies substantially in proportion to the oxygen concentration in the exhaust gas under a condition of a constant temperature. Thus, the pump current can be also used for the detection of the air/fuel ratio.

In this type of oxygen concentration sensor, if an excessive current is supplied to the oxygen pump element, it causes the blackening phenomenon by which the oxygen ions are removed from the solid electrolyte members. For instance, when zirconium dioxide ($ZrO_2$) is used as the solid electrolyte, the oxygen ions $O_2$ are taken from the zirconium dioxide ($ZrO_2$) and zirconium ($Zr$) is separated out. As a result of this blackening phenomenon, the deterioration of the oxygen pump element takes place rapidly, to cause a debasement of the operation of the oxygen concentration sensor as a whole. Therefore, the pump current value must be controlled to be lower than values in a region of generation of the blackening phenomenon (blackening phenomenon generation region) so as to prevent the blackening phenomenon before it is generated.

FIG. 1 shows lines indicating the pump current to the oxygen pump element versus oxygen concentration relation and a boundary line of the generation of the blackening phenomenon with respect to different values of the voltage Vs developing at the sensor cell element, which voltage functions as a parameter. As illustrated, magnitude of the current $I_p$ varies in proportion to the oxygen concentration, and the rate of variation is different for several different values of the voltage $V_s$. In other words, the voltage $V_s$ is a parameter which determines the relation between the magnitude of the current $I_p$ and the oxygen concentration. As illustrated in this figure, the boundary line of the generation of the blackening phenomenon is shown, like the relation between the pump current and the oxygen concentration, as a first-degree function of the oxygen concentration value. Therefore, whether or not the pump current value belongs to values in the blackening phenomenon generation region can be determined from the value of the voltage Vs. Therefore, if the voltage Vs exceeds a predetermined voltage, it can be considered that the value of the pump current is approaching to the region of the generation of the blackening phenomenon, and the generation of the blackening phenomenon can be prevented by reducing the pump current. However, it is recognized that the internal resistance of the oxygen pump element becomes large when the temperature of the oxygen pump element is low. Therefore, under such a condition, the pump current value generating the blackening phenomenon becomes lower than the case in which the temperature of the pump element is high. This means that there is a chance of the generation of the blackening phenomenon even if the voltage Vs is lower than the predetermined voltage.

OBJECT AND SUMMARY OF THE INVENTION

An object of the present invention is therefore to provide an oxygen concentration sensing apparatus by which the generation of the blackening phenomenon when the temperature of the elements is low is surely prevented, and the oxygen concentration is detected accurately.

According to the present invention, an oxygen concentration sensing apparatus comprises:

an oxygen sensing unit being sensitive to oxygen in a gas under measurement and operative to produce an output signal having a magnitude proportional to the concentration of oxygen in the gas under measurement when contacted by a stream of the gas and having a sensor cell element made of a first active plate of an oxygen ion conductive solid electrolyte and a first pair of electrodes sandwiching the active plate, an oxygen pump element made of a second active plate of an oxygen-ion conductive solid electrolyte and a second pair of electrodes sandwiching the active plate, the first and second active plates confronting a restricted region into which the gas under measurement is introduced;

current supply means for supplying a pump current across the second pair of electrodes of the oxygen pump element;

limit voltage setting means for setting a limit voltage in response to a voltage across the second pair of electrodes of the oxygen pump element; and limit means for reducing the pump current supplied across the second pair of electrodes of the oxygen pump element when a voltage generated across the first pair of electrodes of the sensor cell element exceeds limit voltage set by the limit voltage setting means.

In short, a limit voltage is set according to a voltage across the electrodes of the oxygen pump element, and the pump current supplied across the electrodes of the oxygen pump element is reduced when a voltage generated across the electrodes of the sensor cell element has exceeded the limit voltage.

DETAILED DESCRIPTION OF THE PREFERRED EMBODIMENT

An embodiment of the present invention will be explained with reference to the accompanying drawings.

Figure 1:
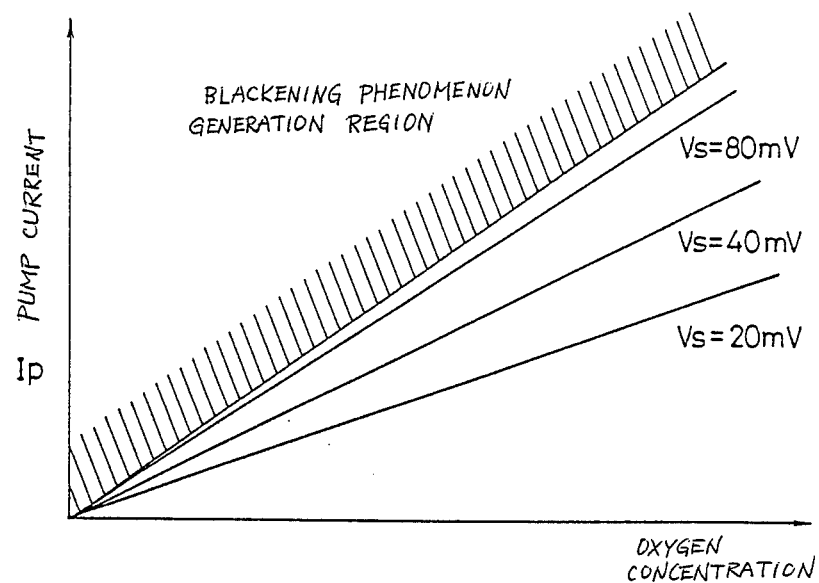
FIG. 1 is a diagram illustrating lines representing oxygen concentration versus pump current charateristic and a boundary of generation of the blackening phenomenon.
Figure 2:
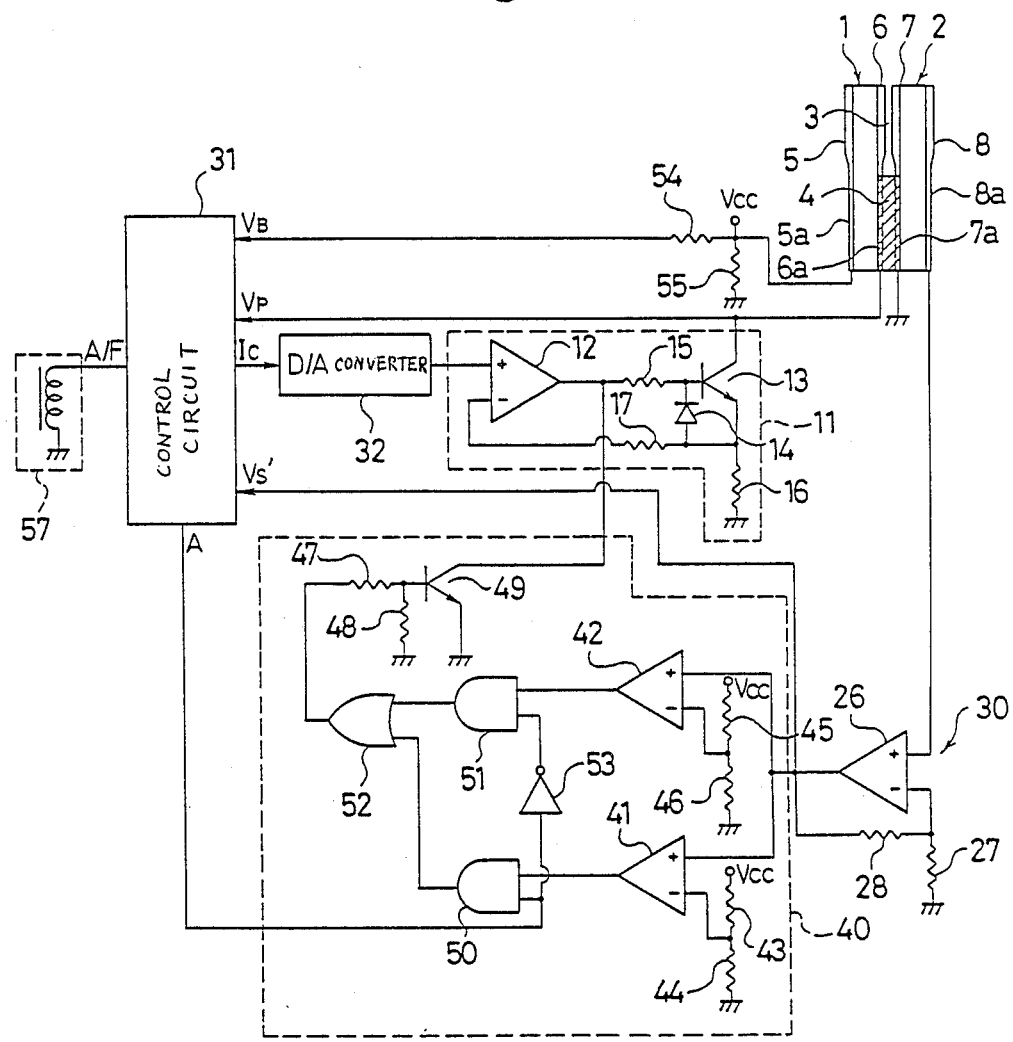
FIG. 2 is a circuit diagram of an embodiment of the oxygen concentration sensing apparatus according to the present invention.

FIG. 2 shows an example of an air/fuel ratio control system in which the oxygen concentration sensing apparatus according to the present invention is utilized. In this system, the oxygen concentration sensing device which is made up of a pair of flat active elements, namely an oxygen pump element 1 and a sensor cell element 2 arranged in parallel to each other, is mounted in an exhaust pipe (not shown) of an internal combustion engine. The main portions of the oxygen pump element 1 and the sensor cell element 2 are made of an oxygen-ion conductive solid electrolyte member. An end portion of the oxygen pump element 1 and an end portion of the sensor cell element 2 which face each other are spaced apart so as to form a gap portion (or a restricted region) 3 between them. The other end portions of the oxygen pump element 1 and the sensor cell element 2 are connected to each other by means of a spacer 4. The oxygen pump element 1 and the sensor cell element 2 are provided with, at their free end portions and on both sides thereof, square electrodes 5 through 8 which are made of a porous heat-proof metal. Further, lead wires 5a through 8a of the square electrodes 5 through 8 respectively, are provided on both surfaces of the connected end portions of the oxygen pump element 1 and the sensor cell element 2. The square electrodes 6 and 7 are located in the inner sides of the oxygen pump element 1 and the sensor cell element 2 facing the gap portion 3. Therefore, they are also referred to as inner electrodes. Similarly, the square electrodes 5 and 8 located in the outer sides of the oxygen pump element 1 and the sensor cell element 2 are also referred to as outer electrodes.

Across the electrodes 5 and 6 of the oxygen pump element 1, a constant current is supplied from a constant current source 11. The current source 11 is constructed as an absorption type circuit, and made up of an operational amplifier 12, an NPN transistor 13, a diode 14, and resistors 15 through 17. More particularly, an output terminal of the operational amplifier 12 is connected to the base of the transistor 13 via the resistor 15. The emitter of the transistor 13 is connected to the ground via the resistor 16, and connected to the inverting input terminal of the operational amplifier 12 through the resistor 17, and further connected to the output terminal of the operational amplifier 12 through the diode 14 which is disposed in a forward direction. The collector of the transistor 13 is connected to the inner electrode 6 of the oxygen pump element 1 through the lead wire 6a. The outer electrode 5 of the oxygen pump element 1 is supplied with a voltage Vcc through the lead wire 5a.

On the other hand, the inner electrode 7 of the sensor cell element 2 is grounded through the lead wire 7a, and the outer electrode 8 of the sensor cell element 2 is connected, through the lead wire 8a, to a non-inverting amplifier 30 which is made up of an operational amplifier 26 and resistors 27 and 28. An output terminal of the non-inverting amplifier 30 is connected to a Vs' input terminal of a control circuit 31. An $I_c$ control output terminal of the control circuit 31 is connected to a D/A converter 32 which, in turn, generates voltage corresponding to a digital data provided at the Ic control output terminal of the control circuit 31. The output terminal of the D/A converter 32 is connected to the non-inverting input terminal of the operational amplifier 12.

A limiter circuit 40 is connected to an output terminal of the non-inverting amplifier 30. The limiter circuit 40 is made up of operational amplifiers 41 and 42, resistors 43 through 48, an NPN transistors 49, AND circuits 50, 51, an OR circuit 52, and a NOT circuit 53. The operational amplifiers 41 and 42 respectively operate as a comparator. The operational amplifier 41 compares an output voltage of the non-inverting amplifier 30 with a voltage divided signal Va of the voltage Vcc obtained by the resistors 43 and 44. An output terminal of the operational amplifier 41 is connected to the AND circuit 50. The AND circuit 50 generates a logical product between the output level of the operational amplifier 41 and the level of a control signal output at a terminal A of the control circuit 31. On the other hand, the operational amplifier 42 compares the output voltage of the non-inverting amplifier 30 with a voltage divided signal Vb (Va<Vb) of the voltage Vcc obtained by the resistors 45 and 46. An output terminal of the operational amplifier 42 is connected to the AND circuit 51. The AND circuit 51 generates a logical product between the output level of the operational amplifier 42 and an inverted level of the level of the control signal output from the output terminal A of the control circuit A, obtained by the NOT circuit 53. By the OR circuit 52, a logical sum between the output levels of the AND circuits 50 and 51 is obtained. An output terminal of the OR circuit 52 is connected to the base of the transistor 49 through a voltage dividing circuit made up of the resistors 47 and 48. The emitter of the transistor 49 is grounded and its collector is connected to an output line of the operational amplifier 12 of the constant current circuit 11.

The control circuit 31 includes a microcomputer, for example, and has an A/F drive terminal, a $V_B$ input terminal and a $V_P$ input terminal in addition to the above mentioned Ic output terminal, A output terminal, and the Vs' input terminal. A solenoid valve 57 for controlling the supply of the secondary air is connected to the A/F drive terminal. The solenoid valve 57 is provided in an air intake side secondary air supply passage which connects to an intake air passage of the engine, at a position downstream of the throttle valve of a carburetor. A voltage divided signal of the voltage Vcc obtained by the resistors 54 and 55 is supplied to the $V_B$ input terminal of the control circuit 31. Also, the $V_P$ input terminal is connected to the lead wire 6a of the oxygen pump element 1.

With this circuit construction, when the digital signal is supplied from the Ic output terminal of the control circuit 31 to the D/A converter 32, the digital signal is converted to a voltage at the D/A converter 32, and this converted voltage is in turn supplied to the non-inverting input terminal of the operational amplifier 12 as a reference voltage Vr1. The pump current value $I_P$ of the pump current flowing across the electrodes of the electrodes 5 and 6 of the oxygen pump element 1 under the supply of the reference voltage Vr1 is detected as a terminal voltage Vx of the resistor 16. This terminal voltage Vx is supplied to the inverting input terminal of the operational amplifier 12 through the resistor 17. When the terminal voltage Vx is lower than the reference voltage Vr1, the output level of the operational amplifier turns to the high level, to increase the base current of the transistor 13. Therefore, the pump current increases. On the other hand, when the terminal voltage Vx is larger than the reference voltage Vr1, the output level of the operational amplifier 12 turns to the low level, to decrease the base current of the transistor 13. Since these operations are repeated at a high speed, the magnitude of the pump current is controlled at a constant current value according to the reference voltage Vr1.

On the other hand, a voltage Vs appears across the electrodes 7 and 8 of the sensor cell element 2. The voltage Vs is supplied to the non-inverting amplifier 30 in which this voltage Vs is amplified, and the amplified voltage is in turn supplied to the Vs' input terminal of the control circuit 31 as the oxygen concentration detection signal. At predetermined intervals, the control circuit 31 detects whether or not the output voltage Vs' is greater than a reference voltage Vr2 corresponding to a target air/fuel ratio. If Vs'>Vr2, it is determined that the air/fuel ratio of the mixture supplied to the engine is rich, and the solenoid valve 57 is driven in an opening direction, so that the secondary air is supplied to the engine. If Vs'≦Vr2, it is determined that the air/fuel ratio of the mixture supplied to the engine is lean, and the drive of the solenoid valve 57 in the opening direction is stopped, so that the supply of the secondary air is stopped.

Figure 3:
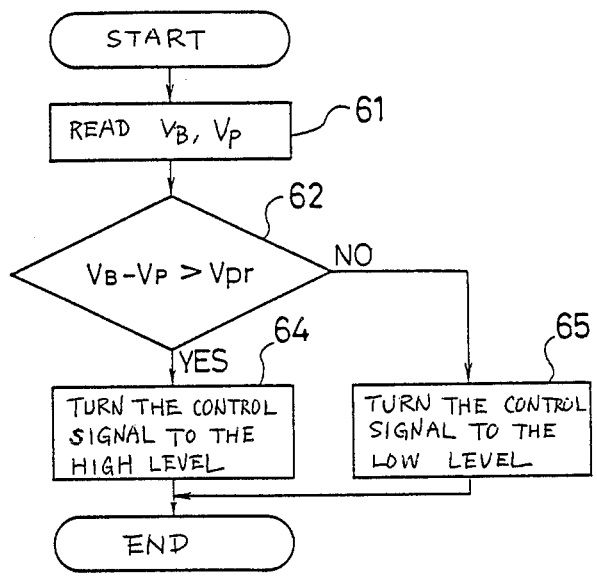
FIG. 3 is a flowchart showing the operation of the control circuit.

As shown in FIG. 3, at the predetermined intervals, the control circuit 31 reads the voltage $V_B$ supplied to the $V_B$ input terminal and the voltage $V_P$ supplied to the $V_P$ input terminal respectively, at a step 61. Then the control circuit 31 calculates a voltage difference between the voltages $V_B$ and $V_P$, and detects whether or not the voltage difference is larger than the predetermined voltage $V_{Pr}$, at a step 62. The voltage $V_P$ represents the voltage at the electrode 6 of the oxygen pump element, and the voltage difference $V_B-V_P$ represents the voltage across the electrodes 5 and 6 of the oxygen pump element 1. If $V_B-V_P>V_{Pr}$, the control signal level at the A output terminal is turned to the high level, at a step 64, in order to set the limit voltage of the voltage Vs at a low level. IF $V_B-V_P≦V_{Pr}$, the control signal level at the A output terminal is turned to the low level, at the step 65, in order to set the limit voltage of the voltage Vs at a high level.

When the voltage Vs across the electrodes 7 and 8 of the sensor cell element 2 rises, the output voltage Vs' of the non-inverting amplifier 30 rises as well. When the voltage Vs exceeds a first limit voltage (50 mV, for example) the voltage Vs' exceeds the voltage divided signal Va obtained by the resistors 43 and 44, and the output voltage of the operational amplifier 41 turns from a low level to the high level. On the other hand, when the voltage Vs exceeds a second limit voltage (60 mV, for example), the voltage Vs' exceeds the voltage divided signal Vb obtained by the resistors 45 and 46, and the output voltage of the operational amplifier 42 turns from a low level to the high level.

When the level of the control signal output from the A output terminal of the control circuit 31 is at the low level, the output signal level of the AND circuit 50 is at the low level irrespectively of the output signal level of the operational amplifier 41. Under this condition, the output signal level of the NOT circuit 53 turns to the high level, and the output signal level of the AND circuit 51 becomes equal to the output signal level of the operational amplifier 42. If the voltage Vs' exceeds the voltage divided signal Vb by the resistors 45 and 46, the output signal level of the operational amplifier 42 turns from the low level to the high level and this high level output signal of the operational amplifier 42 is transmitted to the OR circuit 52 through the AND circuit 51, and the output signal level of the OR circuit 52 turns to the high level.

On the other hand, when the level of the control signal output from the A output terminal of the control circuit 31 is at the high level, the output signal level of the AND circuit 50 becomes equal to the output signal level of the operational amplifier 41, and the output signal level of the NOT circuit 53 becomes equal to the low level. Thus, the output signal level of the AND circuit 51 is at the low level irrespectively of the output signal level of the operational amplifier 42. Therefore, if the voltage Vs' exceeds the voltage divided signal Va obtained by the resistors 43 and 44, and the output signal level of the operational amplifier 41 turns from the low level to the high level, this high level output signal is supplied to the OR circuit 52 through the AND circuit 50, and the output signal level of the OR circuit 52 will be at the high level.

When the output signal level of the OR circuit 52 turns to the high level in this way, the transistor 49 turns on by this high level signal, and the output line of the operational amplifier 12 of the constant current circuit 11 is controlled to be at the earth level. Therefore, the transistor 13 turns off, and the pump current decreases immediately. The generation of the blackening phenomenon can be prevented in this way.

During the warm up period of the engine, the temperature of the oxygen pump element 1 and the sensor cell element 2 is low. Therefore, the internal impedance of the oxygen pump element becomes high, and the voltage applied across the electrodes 5 and 6 of the oxygen pump element 1 goes up. However, this causes a condition in which $V_B - V_P > V_{Pr}$, and the level of the control signal turns to the high level. Therefore, the pump current decreases when the output level of the operational amplifier 41 is at the high level, i.e., when the voltage Vs has exceeded the first limit voltage.

On the other hand, when the engine has warmed up, or when the temperature of the oxygen pump element and the sensor cell element has risen by the heating operation of the heater element, the internal impedance of the oxygen pump element descreases, and the voltage applied across the electrodes 5 and 6 of the oxygen pump element 1 goes down. This will cause a condition in which $V_B - V_P \leq V_{Pr}$, and the level of the control signal will be at the low level. Therefore, the pump current decreases when the output signal level of the operational amplifier 42 is at the high level, i.e., the voltage Vs has exceeded the second limit voltage.

Figure 4:
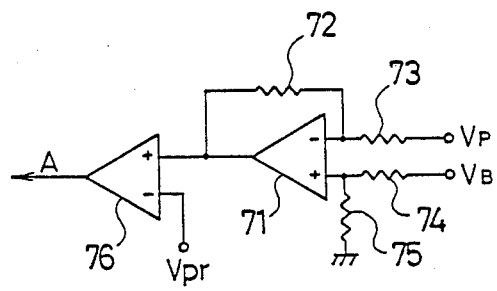
FIG. 4 is a circuit diagram showing another circuit construction for obtaining the operation shown in FIG. 3.

FIG. 4 shows an example of a circuit for performing the operation of the control circuit 31 explained above by the hardware. In this circuit, the voltage difference between the voltage $V_B$ and the voltage $V_P$ is obtained by a differential amplifier including an operational amplifier 71 and resistors 72 through 75. An output voltage of the differential amplifier is compared with the reference voltage $V_{Pr}$ at a comparator which comprises an operational amplifier 76. The control signal is produced as an output signal of this comparator.

In the above description, the present invention has been explained with reference to the embodiment in which the present invention is applied to a sensor of oxygen concentration proportional voltage detection type in which the oxygen concentration detection value is obtained from the voltage generated at the sensor cell element while the pump current supplied to the oxygen pump element is maintained constant. However, it is to be noted that the present invention is applicable to an oxygen concentration sensor of oxygen concentration proportional current detection type in which the oxygen concentration detection value is obtained from the pump current value while the pump current value is controlled so that the voltage generated by the sensor cell element is maintained constant.

It will be appreciated from the foregoing, in the oxygen concentration sensing apparatus according to the present invention, the limit voltage is determined according to the voltage across the electrodes of the oxygen pump element. The supply of the current across the electrodes of the oxygen pump element is decreased when the voltage generated across the electrodes of the sensor cell element exceeds the limit voltage. Therefore, the blackening phenomenon under a low temperature condition of the oxygen pump element, which can be generated at the lower level of the voltage generated across the electrodes of the sensor cell element as compared with a high temperature condition of the oxygen pump element, is surely prevented by setting the limit voltage at a low level.

What is claimed is:

1. An oxygen concentration sensing apparatus comprising:
   an oxygen sensor sensitive to oxygen in a gas under measurement and operative to produce an output signal having a magnitude proportional to the concentration of oxygen in the gas under measurement when contacted by a stream of the gas and having,
   a sensor cell element made of a first active plate of an oxygen ion conductive solid electrolyte and a first pair of electrodes sandwiching said first active plate, and
   an oxygen pump element made of a second active plate of an oxygen ion conductive solid electrolyte and a second pair of electrodes sandwiching said second active plate,
   said first and second active plates confronting a restricted region into which said gas under measurement is introduced;
   current supply means for supplying a pump current across said second pair of electrodes of said oxygen pump element;
   limit voltage setting means for setting a limit voltage in response to a monitored voltage across said second pair of electrodes of said oxygen pump element; said monitored voltage indicating an internal resistance of said oxygen pump element, said limit voltage setting means reducing said limit voltage when said monitored voltage is higher than a predetermined reference voltage to prevent blackening at low temperature levels and
   limit means for reducing the pump current supplied across said second pair of electrodes of said oxygen pump element when a voltage generated across said first pair of electrodes of said sensor cell element exceeds said limit voltage set by said limit voltage setting means.

2. An oxygen concentration sensing apparatus as set forth in claim 1, wherein said limit voltage setting means develops one of two different voltages as said limit voltage in dependence upon whether said monitored voltage across said second pair of electrodes of said oxygen pump element exceeds the predetermined reference voltage.

* * * * *